(12) United States Patent
Sensenbrenner et al.

(10) Patent No.: US 8,187,272 B2
(45) Date of Patent: May 29, 2012

(54) SURGICAL INSTRUMENT FOR COAGULATION AND SUCTION

(75) Inventors: Alexander Sensenbrenner, Crestline, CA (US); Dale Rice, Pacific Palisades, CA (US)

(73) Assignee: Biomedcraft Designs, Inc., Crestline, CA (US)

( * ) Notice: Subject to any disclaimer, the term of this patent is extended or adjusted under 35 U.S.C. 154(b) by 1123 days.

(21) Appl. No.: 11/544,250

(22) Filed: Oct. 6, 2006

(65) Prior Publication Data

US 2008/0086121 A1    Apr. 10, 2008

(51) Int. Cl.
*A61B 18/14* (2006.01)
(52) U.S. Cl. ............... 606/50; 606/41; 606/45
(58) Field of Classification Search .......... 606/41–50
See application file for complete search history.

(56) References Cited

U.S. PATENT DOCUMENTS

| | | | |
|---|---|---|---|
| 3,828,780 A | 8/1974 | Morrison, Jr. | |
| 5,084,045 A * | 1/1992 | Helenowski | 606/32 |
| 5,122,138 A * | 6/1992 | Manwaring | 606/46 |
| 5,195,959 A | 3/1993 | Smith | |
| 5,282,799 A * | 2/1994 | Rydell | 606/48 |
| 5,814,044 A | 9/1998 | Hooven | |
| 5,972,416 A | 10/1999 | Reimels et al. | |
| 5,989,249 A | 11/1999 | Kirwan, Jr. | |
| 6,086,583 A * | 7/2000 | Ouchi | 606/41 |
| 6,102,885 A * | 8/2000 | Bass | 604/22 |
| 6,183,469 B1 * | 2/2001 | Thapliyal et al. | 606/41 |
| 6,346,107 B1 * | 2/2002 | Cucin | 606/49 |
| 6,352,533 B1 * | 3/2002 | Ellman et al. | 606/41 |
| 6,379,350 B1 | 4/2002 | Sharkey et al. | |
| 6,379,351 B1 * | 4/2002 | Thapliyal et al. | 606/41 |
| 6,395,002 B1 | 5/2002 | Ellman et al. | |
| 6,432,105 B1 | 8/2002 | Ellman et al. | |
| 6,485,490 B2 * | 11/2002 | Wampler et al. | 606/48 |
| 6,572,614 B1 | 6/2003 | Ellman et al. | |
| 6,616,656 B2 | 9/2003 | Brommersma | |
| 6,620,156 B1 | 9/2003 | Garito et al. | |
| 6,749,604 B1 | 6/2004 | Eggers et al. | |
| 6,758,846 B2 | 7/2004 | Goble et al. | |
| 6,840,937 B2 | 1/2005 | Van Wyk | |
| 6,893,435 B2 | 5/2005 | Goble | |
| 6,893,440 B2 | 5/2005 | Durgin et al. | |
| 6,918,880 B2 * | 7/2005 | Brookner et al. | 600/565 |
| 6,918,906 B2 | 7/2005 | Long | |
| 7,041,102 B2 | 5/2006 | Truckai et al. | |
| 7,083,615 B2 | 8/2006 | Peterson et al. | |
| 7,083,619 B2 | 8/2006 | Truckai et al. | |
| 2004/0002664 A1 * | 1/2004 | Brookner et al. | 600/565 |
| 2005/0267446 A1 * | 12/2005 | Cucin | 604/542 |
| 2006/0079879 A1 * | 4/2006 | Faller et al. | 606/40 |

OTHER PUBLICATIONS

Search Report/Written Opinion for corresponding PCT application, PCT/US07/21395 mailed Apr. 7, 2008 (8 pgs.).
International Preliminary Report on Patentability (Chapter 1 of the Patent Cooperation Treaty), mailed Apr. 7, 2009 in the corresponding PCT application (PCT/US2007/021385) (6 pgs.).

* cited by examiner

*Primary Examiner* — Linda Dvorak
*Assistant Examiner* — Amanda Scott
(74) *Attorney, Agent, or Firm* — Jackson Walker L.L.P.; Christopher J. Rourk

(57) ABSTRACT

An apparatus for aiding coagulation of fluids and tissue during surgery is provided. The apparatus includes a suction tube and first and second electrodes shaped as a cylindrical section extending from the suction tube. Two spaces are formed between the first electrode and the second electrode, and the distance between the tips of the electrodes and the suction tube is large enough to allow unobstructed viewing of the tissue that is being treated.

20 Claims, 4 Drawing Sheets

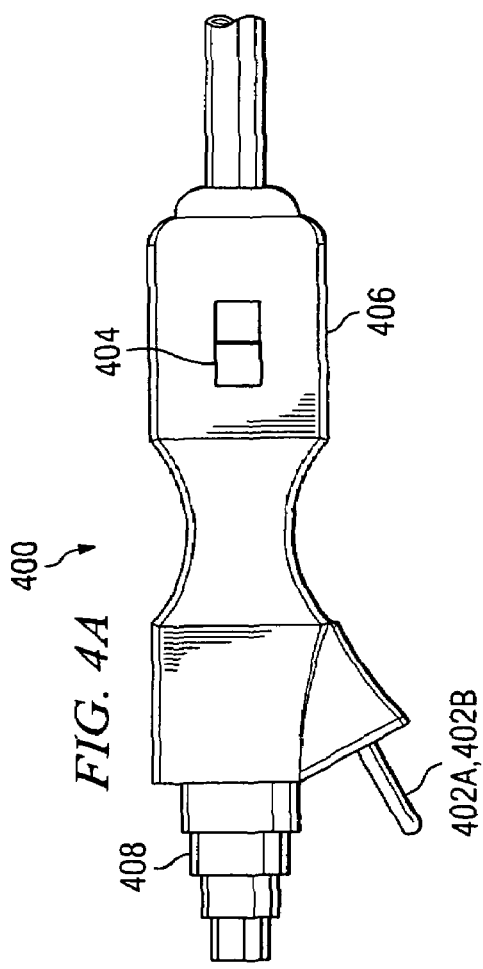
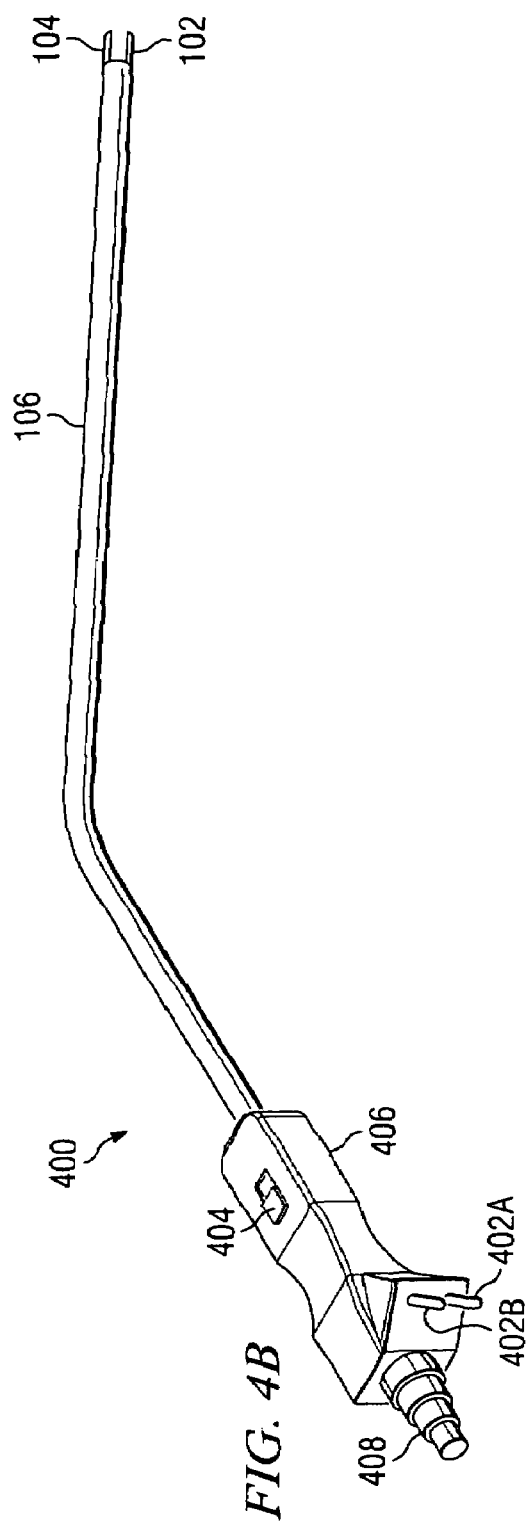
FIG. 4A
FIG. 4B

SURGICAL INSTRUMENT FOR COAGULATION AND SUCTION

FIELD OF THE INVENTION

The present invention relates to electrosurgical coagulation instruments and systems for treating human or animal biological tissue using radio-frequency energy. More specifically, the present invention relates to surgical devices and methods for applying radio-frequency energy to coagulate blood and desiccate tissues in combination with the facility to suction fluids and suspended materials from the surgical site.

BACKGROUND OF THE INVENTION

Numerous surgical instruments for the treatment of biological tissues through the application of energy in medical procedures are known in the art. Such prior art devices use wire-loop electrodes shaped to enhance current density where employed, resulting in high power densities in the affected tissues. These prior art devices are adapted to cause tissue ablation by burning, cauterization, or otherwise damaging the tissue. While such devices are useful for such purposes, they have no other recognized uses.

SUMMARY OF THE INVENTION

In accordance with the present invention, a surgical instrument is provided that allows tissue to be treated to coagulate bodily fluids during surgery using radio frequency electrical energy.

In accordance with an exemplary embodiment of the present invention, an apparatus for aiding coagulation of fluids in tissue during surgery is provided. The apparatus includes a suction tube and first and second electrodes shaped as a cylindrical section extending from the suction tube. Two spaces are formed between the first electrode and the second electrode, and the distance between the tips of the electrodes and the suction tube is large enough to allow unobstructed viewing of the tissue that is being treated.

The present invention provides many important technical advantages. One important technical advantage of the present invention is a surgical instrument that allows tissue to be treated with radio frequency energy in a manner that does not obstruct viewing of the tissue during treatment and which allows gasses, particulates and fluids to be removed.

Those skilled in the art will further appreciate the advantages and superior features of the invention together with other important aspects thereof on reading the detailed description that follows in conjunction with the drawings.

BRIEF DESCRIPTION OF THE DRAWINGS

FIG. 4 is a diagram of two views A and B of a connector for a surgical instrument in accordance with an exemplary embodiment of the present invention;

DETAILED DESCRIPTION OF PREFERRED EMBODIMENTS

Figure 1:
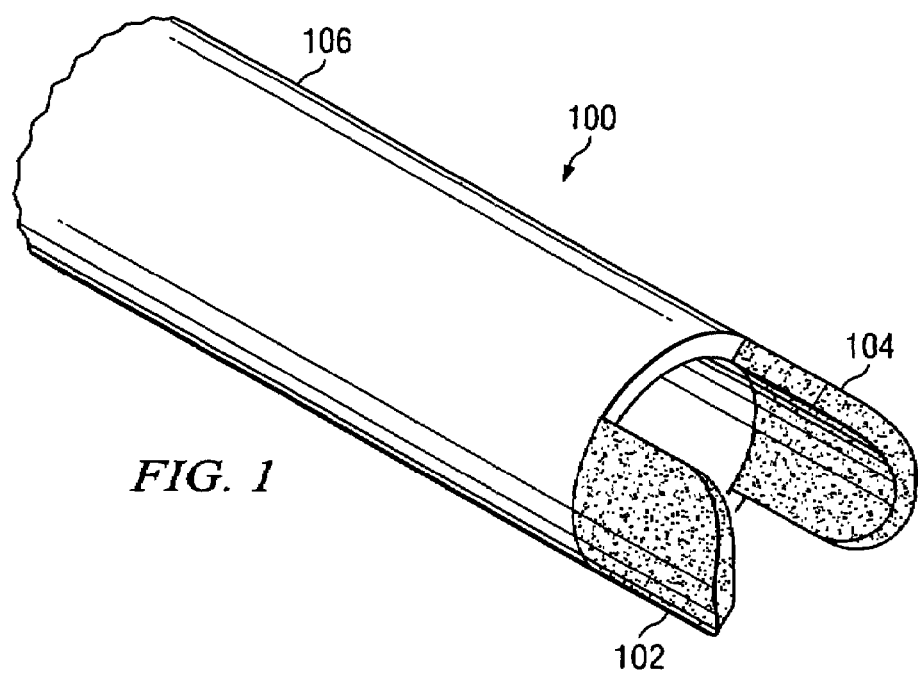
FIG. 1 is a diagram of a surgical instrument for coagulating blood and providing suction in accordance with an exemplary embodiment of the present invention.

In the description that follows, like parts are marked throughout the specification and drawings with the same reference numerals. The drawing figures might not be to scale and certain components can be shown in generalized or schematic form and identified by commercial designations in the interest of clarity and conciseness.

FIG. 1 is a diagram of a surgical instrument 100 for coagulating blood and providing suction in accordance with an exemplary embodiment of the present invention.

Surgical instrument 100 coagulates bleeding wounds while providing a mechanism for removing gaseous, particulate solids and liquids, such as serous materials, from the site of treatment. Surgical instrument 100 includes electrodes 102 and 104, which are rounded or chamfered so as to provide adequate current distribution and sufficient surface area in order to reduce or eliminate the high power densities that produce char and smoke, the products of vaporization and ablation. Electrodes 102 and 104 are set in relationship to each other to reduce electrode to electrode current flow and to promote a current pathway through the target tissues. Electrodes 102 and 104 are of sufficient prominence as to allow for the shallow angles of incidence demanded by tight spaces. Surgical instrument 100 delivers lower levels of energy over an area larger than those depicted in prior art with the intent of keeping tissue temperatures below 200 degrees Centigrade, ideally below 120 degrees Centigrade to avoid charring and collateral damage to adjacent tissues and structures.

In addition, electrodes 102 and 104 support suction tube 106 away from the tissue that is being treated while allowing visual access to the tissue, so as to allow the practitioner that is using surgical instrument 100 to be able to determine whether the tissue has been sufficiently coagulated, whether tissue charring is occurring, or whether other treatment is required. The structure of electrodes 102 and 104 further provides a channel to help direct the flow of gasses, particulates and fluids into suction tube 106, so as to facilitate coagulation. Suction tube 106 can be constructed of non-conductive materials, can be constructed of metal and a non-conductive tip with electrodes 102 and 104 embedded into it, or can be constructed in other suitable manners. In one exemplary embodiment, suction tube 106 is constructed from metal soft enough to allow for ad hoc bending by the operator during use.

In one exemplary embodiment, the non-conducting surfaces of electrodes 102 and 104 and the inner and outer walls of suction tube 106 can be coated with Teflon™ (PTFE), tungsten disulfide or other "non-stick" coatings, to reduce the need for repeated cleaning of surgical instrument 100 during its use during a procedure. Conductive materials can be disposed in the non-stick coating, the non-stick coating can be applied or treated so as to create small conducting pathways, or other suitable processes can be used to allow the electrodes to conduct electricity with the non-stick coating.

Surgical instrument 100 is compatible with suitable bipolar electrosurgical generators on the market. However, unlike prior art devices that are designed for use with such bipolar electrosurgical generators, which are used to ablate tissue and then suction it away, surgical instrument 100 is optimized to reduce or eliminate tissue destruction. In particular, electrodes 102 and 104 are configured to avoid current concentration, electrical field concentration, power concentration, or other effects that are optimized in prior art system in order to cause tissue ablation, such as by increasing the electrode surface area so as to provide a larger tissue contact area, by electrode shaping, or by other suitable factors. Electrodes 102 and 104 provide uniform current, electrical field, and power so as to aid in coagulation without tissue ablation. Suction is applied primarily to draw away blood, so as to provide a dry field to aid in coagulation. In addition to increasing electrode surface area, lower frequency voltages are applied to reduce tissue ablation and aid in coagulation, the lower limit being determined by the occurrence of muscle stimuli. As such muscle stimuli typically occurs at frequencies below several hundred hertz, and as tissue ablation is typically performed using fundamental frequencies above several hundred kHz, the operator can be given increased selectivity of fundamental frequency control within the range of several hundred to several thousand hertz. Likewise, operator control is provided for voltage levels, current levels, power levels, voltage waveforms, and other operating parameters.

Figure 2:
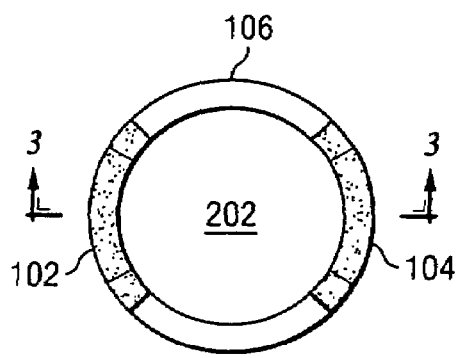
FIG. 2 is a diagram of a front view of a surgical instrument in accordance with an exemplary embodiment of the present invention.

FIG. 2 is a diagram of a front view of surgical instrument 100 in accordance with an exemplary embodiment of the present invention. The curvature of electrodes 102 and 104 is aligned with suction tube 106, so as to facilitate the flow of gasses and fluids through central suction lumen 202. In addition, the shape of electrodes 102 and 104 helps to control the voltage and current distribution in the tissue between the electrodes so as to avoid concentration of heating in tissue.

Figure 3:
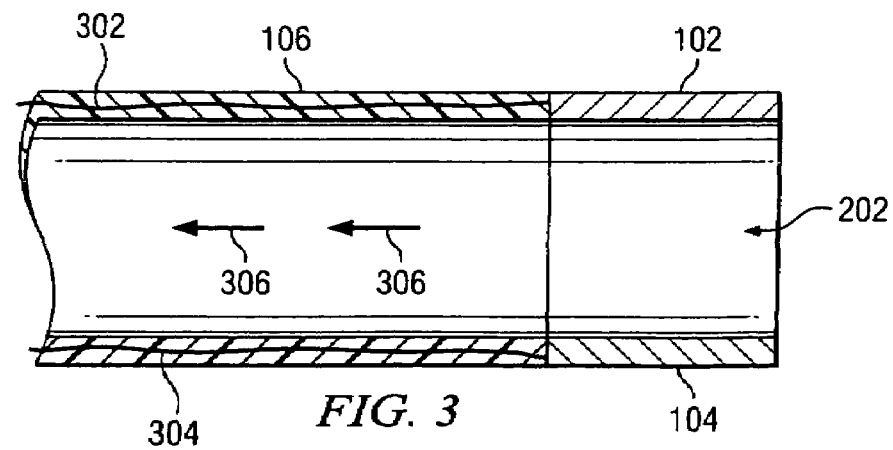
FIG. 3 is a diagram of a section view of a surgical instrument in accordance with an exemplary embodiment of the present invention.

FIG. 3 is a diagram of a section view of surgical instrument 100 in accordance with an exemplary embodiment of the present invention. Embedded conductors 302 and 304 provide electrical current and voltage to electrodes 102 and 104. Suction tube 106 can be fabricated from an insulating material, insulation can be provided for embedded conductors 302 and 304 where suction tube 106 is fabricated from a conducting material, or other suitable configurations can be used to insulate conductors 302 and 304 from suction tube 106 and each other. Gasses, fluids and particulates are conducted in the direction of arrows 306 and are removed to a suitable container.

FIG. 4 is a diagram of two views A and B of a connector 400 for surgical instrument 100 in accordance with an exemplary embodiment of the present invention. Connector 400 includes electrical connectors 402A and 402B, which are electrically connected to conductors 302 and 304. Suction control port 404 allows the amount of suction to be controlled, so as to increase the volume of air for cooling, to adjust the amount of suction based on the amount of gas, particulate solids, or fluids that need to be removed, or for other suitable purposes. Instrument body 406 includes ergonomic grips to allow the user to maintain a firm grip on surgical instrument 100 under moist conditions and to reduce fatigue. Suction tubing connector 408 allows surgical instrument 100 to be connected to a source of suction.

Figure 5:
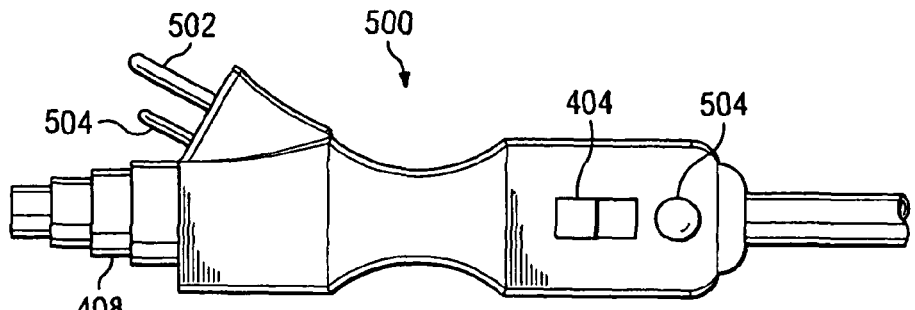
FIG. 5 is a diagram of a connector for a surgical instrument with an electrosurgical generator control in accordance with an exemplary embodiment of the present invention.

FIG. 5 is a diagram of connector 500 for a surgical instrument with electrosurgical generator control in accordance with an exemplary embodiment of the present invention. Connector 500 includes radio frequency current pins 502, which provide radio frequency electrical energy to the electrodes 102 and 104, and electrosurgical generator control pins 504, which allow the operator to control the power delivered to the tissue through the electrodes. In addition, electrosurgical generator control 504 allows the operator to control the application of power to the electrodes 102 and 104. In one exemplary embodiment, electrosurgical generator control 504 can be an on/off switch, a thumb dial, or other suitable controls.

Figure 6:
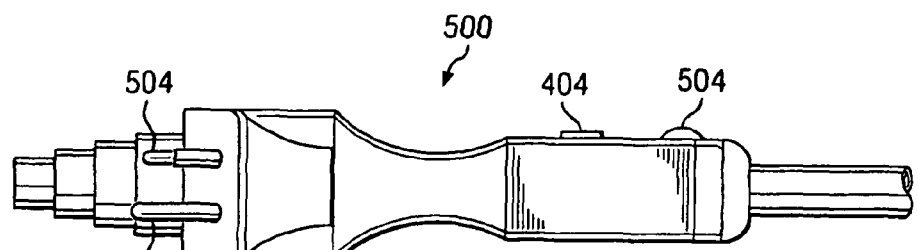
FIG. 6 is an alternate view of a connector for a surgical instrument with an electrosurgical generator control in accordance with an exemplary embodiment of the present invention.

FIG. 6 is alternate view of connector 500 for a surgical instrument with electrosurgical generator control in accordance with an exemplary embodiment of the present invention. As shown in FIG. 6, the radio frequency current pins 502 and electrosurgical generator control pins 504 extend at a right angle to suction port 404 and electrosurgical generator control 504, so as not to interfere with the operation of the controls.

Figure 7A:
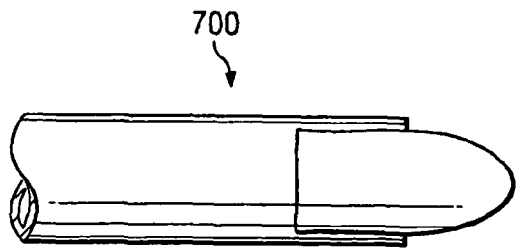
FIG. 7 is a diagram of electrodes in accordance with an exemplary embodiment of the present invention.
Figure 7B:
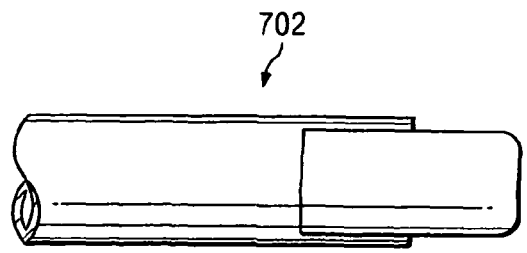

FIG. 7 is a diagram of electrodes 700 and 702 in accordance with an exemplary embodiment of the present invention. Electrodes 700 and 702 have rounded corners so as to avoid concentration points, where current density can cause tissue burning, and to distribute the electrical field generated between the electrodes in a uniform manner.

Figure 8:
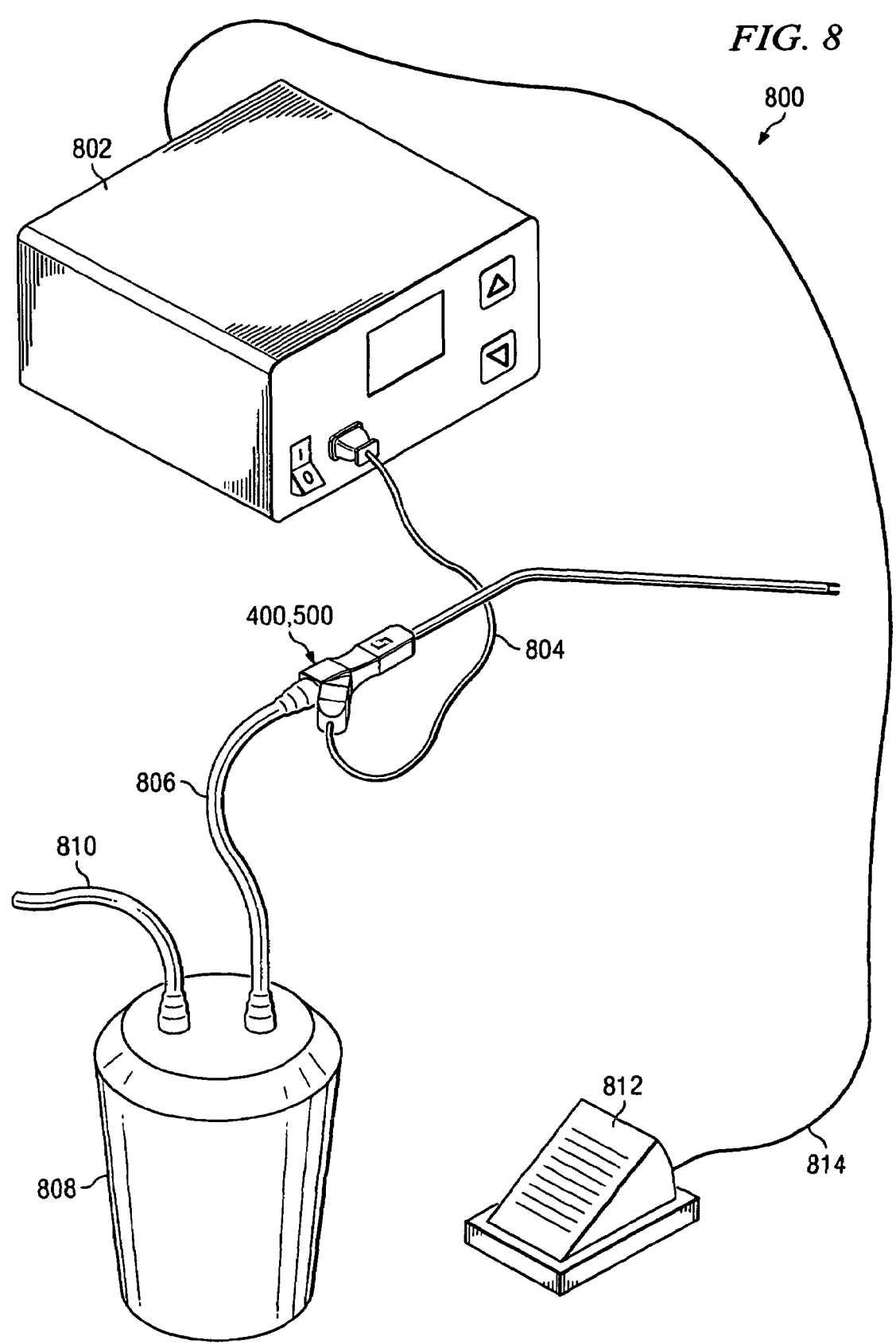
FIG. 8 is a diagram of a system in accordance with an exemplary embodiment of the present invention.

FIG. 8 is a diagram of system 800 in accordance with an exemplary embodiment of the present invention. System 800 includes bipolar generator 802, which is coupled by power cord 804 to connector 400 or 500. A suction tube 806 is also coupled to connector 400 or 500, and carries gaseous, particulate solids and liquids, such as serous materials, from the site of treatment to container 808, which can include baffles, filters, or other suitable materials to prevent such materials from being carried on to a suction generator (not explicitly shown) that is connected to container 808 by suction tube 810. A footswitch 812 can be used by the operator, either alone or in conjunction with electrosurgical generator control 504, to allow the operator to control the power being provided to the treated tissue. In one exemplary embodiment, the footswitch 812 can be used to control power, frequency, voltage, current, waveform, or other suitable variables. For example, footswitch 812 can be configured to allow the operator to control the frequency of the applied electricity from a low of several hundred Hz to a high of several thousand Hz, so as to allow the operator to prevent tissue ablation without causing muscle stimulation. The suction is controlled using the small slot in the top of the instrument.

Although exemplary embodiments of a system and method of the present invention have been described in detail herein, those skilled in the art will also recognize that various substitutions and modifications can be made to the systems and methods without departing from the scope and spirit of the appended claims.

What is claimed is:

1. An apparatus for aiding coagulation of fluids in tissue during surgery comprising;
   a suction structure;
   a first electrode shaped as a U-shaped cylindrical section extending from an end of the suction structure, wherein the first electrode has rounded edges to provide even electric field distribution and to minimize tissue burning;
   a second electrode shaped as a U-shaped cylindrical section extending from an end of the suction structure and opposite from the first electrode, wherein the second electrode has rounded edges to provide even electric field distribution and to minimize tissue burning;
   a first air gap formed by a first circumferential distance between the first electrode and the second electrode, wherein the first circumferential distance is approximately equal to the distance between a tip of the first electrode and the suction structure; and
a second air gap formed by a second circumferential distance between the first electrode and the second electrode, wherein the second circumferential distance is approximately equal to the distance between a tip of the second electrode and the suction structure.

2. The apparatus of claim 1 further comprising a protective coating on a non-conducting surface of the first electrode.

3. The apparatus of claim 1 further comprising an electrical conductor embedded entirely in the suction structure.

4. The apparatus of claim 1 further comprising an electrical conductor embedded in the suction structure, wherein the suction structure comprises an insulating material.

5. The apparatus of claim 1 further comprising an insulated electrical conductor embedded in the suction structure, wherein the suction structure comprises a conducting material.

6. The apparatus of claim 1 further comprising a protective coating on the first and second electrodes, the protective coating having conducting pathways to allow the electrodes to conduct electricity with the protective coating.

7. The apparatus of claim 1 further comprising an ergonomic grip coupled to the suction structure.

8. The apparatus of claim 1 further comprising:
an ergonomic grip coupled to the suction structure; and
a suction control disposed on the ergonomic grip.

9. The apparatus of claim 1 wherein a surface of the first electrode is coated and treated so as to create small conducting pathways through the coating.

10. The apparatus of claim 9 wherein a surface of the second electrode is coated and treated so as to create small conducting pathways through the coating.

11. The apparatus of claim 1, wherein the first electrode has rounded edges that prevent the formation of asperities.

12. A method for aiding coagulation of fluids in tissue during surgery comprising:
applying a first electrode and a second electrode to damaged tissue, each electrode extending from the end of a suction structure having rounded edges and a shape that evenly distributes an electric field, an electric current, and a dissipated power in the damaged tissue;
applying bipolar energy to the tissue so as to aid in coagulation;
limiting the bipolar energy to minimize tissue burning; and
providing suction to induce an air flow to aid coagulation.

13. The method of claim 12 wherein limiting the bipolar energy to avoid charring comprises limiting a fundamental frequency of the bipolar energy to between several hundred and several thousand hertz.

14. An apparatus for aiding coagulation of fluids in tissue during surgery comprising:
a suction structure;
electrode means for aiding coagulation and avoiding tissue ablation, the electrode means having rounded corners and extending from the end of the suction structure;
a bipolar energy source coupled to the electrode means, the bipolar energy source providing alternating frequency power to the electrode means having a fundamental frequency of several hundred to several thousand hertz to prevent tissue ablation
wherein the suction structure is used to provide air flow to facilitate coagulation.

15. The apparatus of claim 14 further comprising an electrical conductor entirely embedded in the suction structure.

16. The apparatus of claim 14 further comprising an electrical conductor embedded in the suction structure, wherein the suction structure comprises an insulating material.

17. The apparatus of claim 14 further comprising an insulated electrical conductor embedded in the suction structure, wherein the suction structure comprises a conducting material.

18. The apparatus of claim 14 further comprising a protective coating on the suction structure.

19. The apparatus of claim 14 further comprising an ergonomic grip coupled to the suction structure.

20. The apparatus of claim 14 further comprising:
an ergonomic grip coupled to the suction structure; and
a suction control disposed on the ergonomic grip.

* * * * *

UNITED STATES PATENT AND TRADEMARK OFFICE
CERTIFICATE OF CORRECTION

PATENT NO.       : 8,187,272 B2                                Page 1 of 1
APPLICATION NO.  : 11/544250
DATED            : May 29, 2012
INVENTOR(S)      : Alexander Sensenbrenner and Dale Rice It is certified that error appears in the above-identified patent and that said Letters Patent is hereby corrected as shown below:

Column 6, line 21, claim 14, add "; and" after "ablation"

Signed and Sealed this
Seventh Day of August, 2012

David J. Kappos
*Director of the United States Patent and Trademark Office*